US010342419B2

(12) United States Patent
Hayashi (10) Patent No.: US 10,342,419 B2
(45) Date of Patent: Jul. 9, 2019

(54) ENDOSCOPE LIGHTING DEVICE (71) Applicant: PANASONIC INTELLECTUAL PROPERTY MANAGEMENT CO., LTD., Osaka (JP)

(72) Inventor: Shintaro Hayashi, Hyogo (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 0 days.

(21) Appl. No.: 15/875,377

(22) Filed: Jan. 19, 2018

(65) Prior Publication Data

US 2018/0206713 A1 Jul. 26, 2018

(30) Foreign Application Priority Data

Jan. 26, 2017 (JP) .................. 2017-012466

(51) Int. Cl.
A61B 1/06 (2006.01)
A61B 1/04 (2006.01)
G02B 23/24 (2006.01)
A61B 1/00 (2006.01)
A61B 1/12 (2006.01)
G02B 6/38 (2006.01)
G02B 23/26 (2006.01)
G02B 6/42 (2006.01)
G02B 6/06 (2006.01)
H04N 5/225 (2006.01)

(52) U.S. Cl.
CPC ........ A61B 1/0661 (2013.01); A61B 1/00126 (2013.01); A61B 1/043 (2013.01); A61B 1/063 (2013.01); A61B 1/0669 (2013.01); A61B 1/128 (2013.01); G02B 6/06 (2013.01); G02B 6/38 (2013.01); G02B 6/3897 (2013.01); G02B 6/4292 (2013.01); G02B 23/2461 (2013.01); G02B 23/2476 (2013.01); G02B 23/26 (2013.01); A61B 1/0011 (2013.01); H04N 2005/2255 (2013.01)

(58) Field of Classification Search
CPC ............ G02B 23/2461; G02B 23/2476; H04N 2005/2255; A61B 1/0661; A61B 1/043; A61B 1/0011
USPC .......................................................... 385/88
See application file for complete search history.

(56) References Cited

U.S. PATENT DOCUMENTS

2009/0040781 A1 2/2009 Ito
2014/0005483 A1* 1/2014 Ohashi ............... A61B 1/00195
600/162
2014/0104578 A1* 4/2014 Madamopoulos ..........................
G03B 21/2033
353/20

FOREIGN PATENT DOCUMENTS

JP 2009-039438 2/2009
JP 2014-167958 9/2014
JP 5682813 3/2015

* cited by examiner

Primary Examiner — Jerry M Blevins
(74) Attorney, Agent, or Firm — Greenblum & Bernstein, P.L.C.

(57) ABSTRACT

An endoscope lighting device to be used for an endoscope is provided. The endoscope lighting device includes a housing. A laser light source is in the housing. A fiber cable receives laser light emitted by the laser light source. A phosphor of a fluorescent light emitter emits fluorescent light using the laser light exiting from the fiber cable. A blower generates airflow in the housing. A shakable body contacts the fiber cable and shakes in reaction to the airflow generated by the blower.

17 Claims, 4 Drawing Sheets

ENDOSCOPE LIGHTING DEVICE

CROSS REFERENCE TO RELATED APPLICATION

This application claims the benefit of priority of Japanese Patent Application Number 2017-012466 filed on Jan. 26, 2017, the entire content of which is hereby incorporated by reference.

BACKGROUND

1. Technical Field

The present disclosure relates to an endoscope lighting device to be used for an endoscope.

2. Description of the Related Art

One of conventionally disclosed lighting devices includes an excitation light source that emits excitation light, a phosphor layer that emits fluorescent light when excited by the excitation light, a condenser lens that allows light to enter the phosphor layer, and a first lens that the fluorescent light emitted by the phosphor layer enters (see, for example, Japanese Patent No. 5682813 (Patent Literature (PTL) 1)).

With a common lighting device, spots called speckles generated by light interference are displayed on the screen. Therefore, in order to inhibit generation of speckles, which cause deterioration in display quality, the lighting device of PTL 1: includes a piezoelectric element that causes a reflective mirror to shake in the thickness direction of the reflective mirror, and a driving device that temporally changes the shape of the reflective surface of the reflective mirror such that the reflective mirror has an undulating reflective surface; and temporally varies the amplitude of the shake of the piezoelectric element using the piezoelectric element and the driving device.

SUMMARY

However, even if the generation of speckles can be inhibited, the use of the piezoelectric element and the driving device results in a rise of the manufacturing cost of the endoscope lighting device. Thus, there is a demand for an endoscope lighting device that inhibits generation of speckles as well as a rise in the manufacturing cost.

In light of this, it is an object of the present disclosure to provide an endoscope lighting device capable of inhibiting generation of speckles while inhibiting a rise in the manufacturing cost of the endoscope lighting device.

In order to achieve the above object, an endoscope lighting device according to an aspect of the present disclosure is an endoscope lighting device to be used for an endoscope and includes: a housing; a laser light source in the housing; a fiber cable that receives laser light emitted by the laser light source; a phosphor that emits fluorescent light using the laser light exiting from the fiber cable; a blower that generates airflow in the housing; and a shakable body that contacts the fiber cable and shakes in reaction to the airflow generated by the blower.

Furthermore, in order to achieve the above object, an endoscope lighting device according to an aspect of the present disclosure is an endoscope lighting device to be used for an endoscope, an includes: a housing; a laser light source in the housing; a fiber cable that receives laser light emitted by the laser light source; a phosphor that emits fluorescent light using the laser light exiting from the fiber cable; and a blower that generates airflow in the housing. The fiber cable is in contact with the blower.

According to the present disclosure, it is possible to inhibit generation of speckles while inhibiting a rise in the manufacturing cost of an endoscope lighting device.

BRIEF DESCRIPTION OF DRAWINGS

The figures depict one or more implementations in accordance with the present teaching, by way of examples only, not by way of limitations. In the figures, like reference numerals refer to the same or similar elements.

DETAILED DESCRIPTION OF THE EMBODIMENTS

Hereinafter, embodiments of the present disclosure will be described with reference to the drawings. Each of the embodiments described below shows one specific example of the present disclosure. Therefore, the numerical values, shapes, materials, structural elements, the arrangement and connection of the structural elements, etc., illustrated in the embodiments below are mere examples, and are not intended to limit the present disclosure. As such, among the structural elements in the embodiments below, structural elements not recited in any one of the independent claims defining the most generic concepts of the present disclosure are described as arbitrary structural elements.

Furthermore, the term "approximately . . . " is intended to mean, in an example case of "approximately the same", not only exactly the same, but also what would be recognized as essentially the same.

Note that each figure is a schematic illustration and not necessarily a precise illustration. Additionally, throughout the figures, structural elements that are essentially the same share like reference signs, and overlapping descriptions thereof are omitted or simplified.

Hereinafter, an endoscope lighting device according to Embodiment 1 of the present disclosure will be described.

Embodiment 1

[Configuration]

Figure 1:
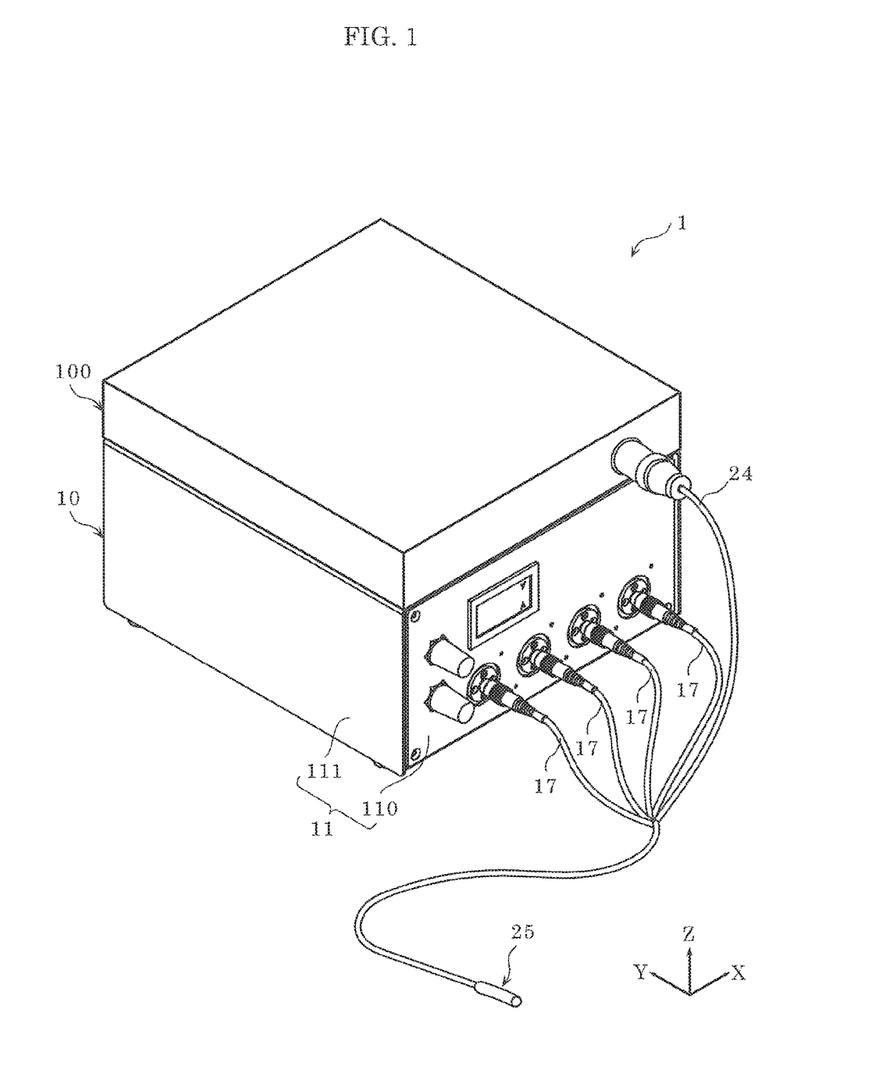
FIG. 1 is a perspective view illustrating an endoscope lighting device according to Embodiment 1.
Figure 2:
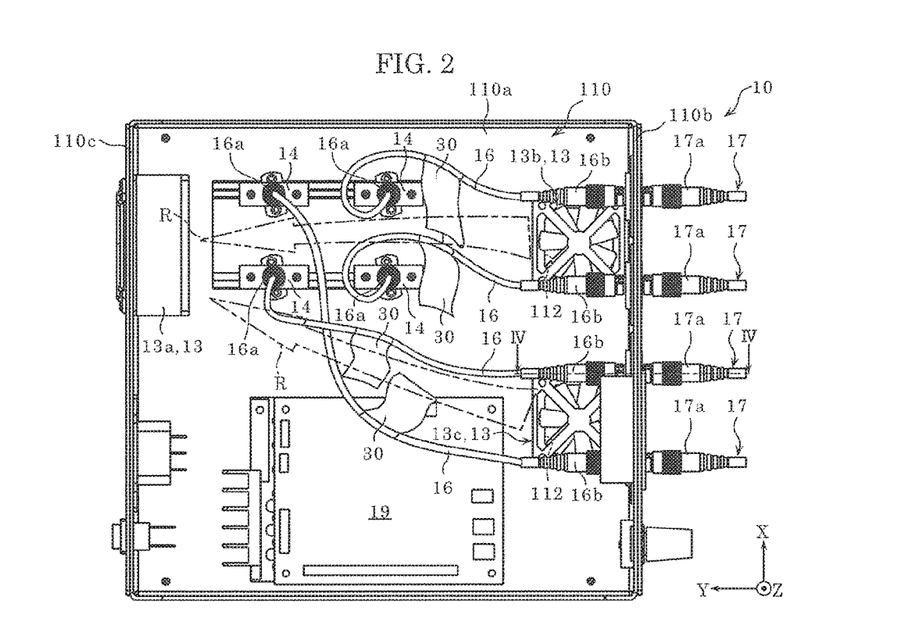
FIG. 2 is a plan view illustrating an inner structure of the endoscope lighting device according to Embodiment 1.
Figure 3:
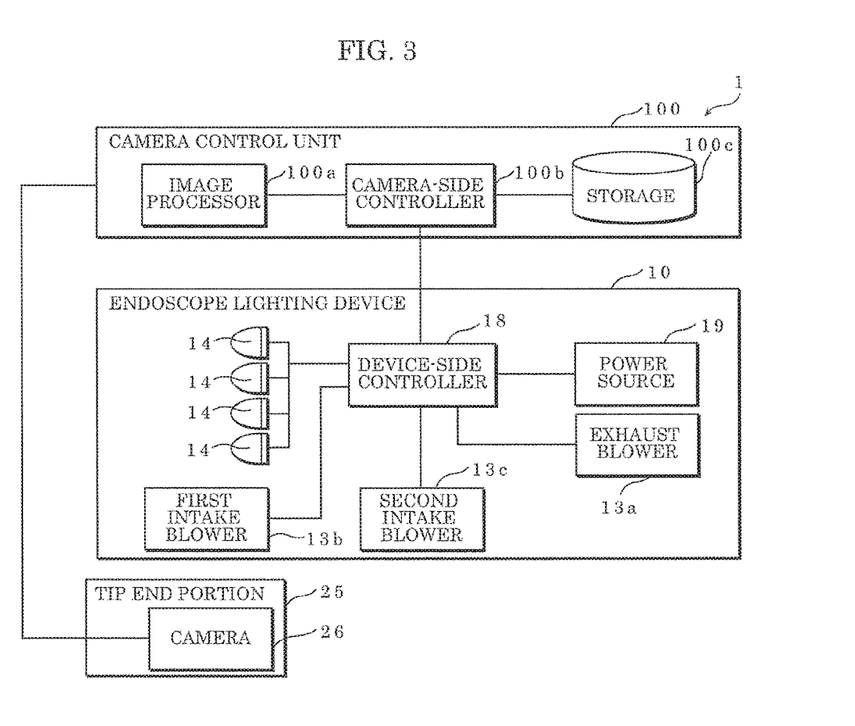
FIG. 3 is a block diagram illustrating the endoscope lighting device according to Embodiment 1.
Figure 4:
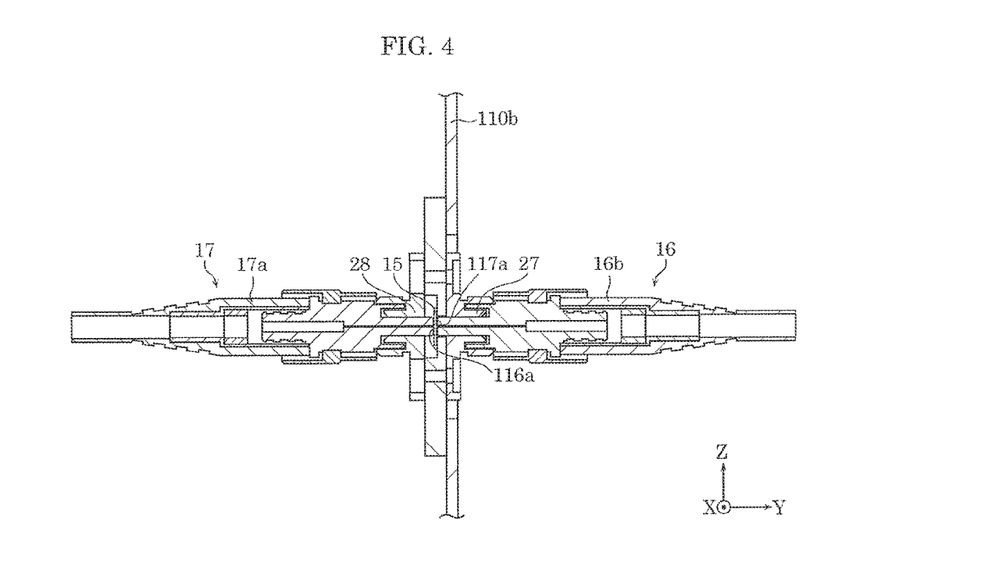
FIG. 4 is a cross sectional view taken along line IV-IV in FIG. 2, illustrating, for example, a first fiber cable, a fluorescent light emitter, and a second fiber cable of the endoscope lighting device according to Embodiment 1.
Figure 5:
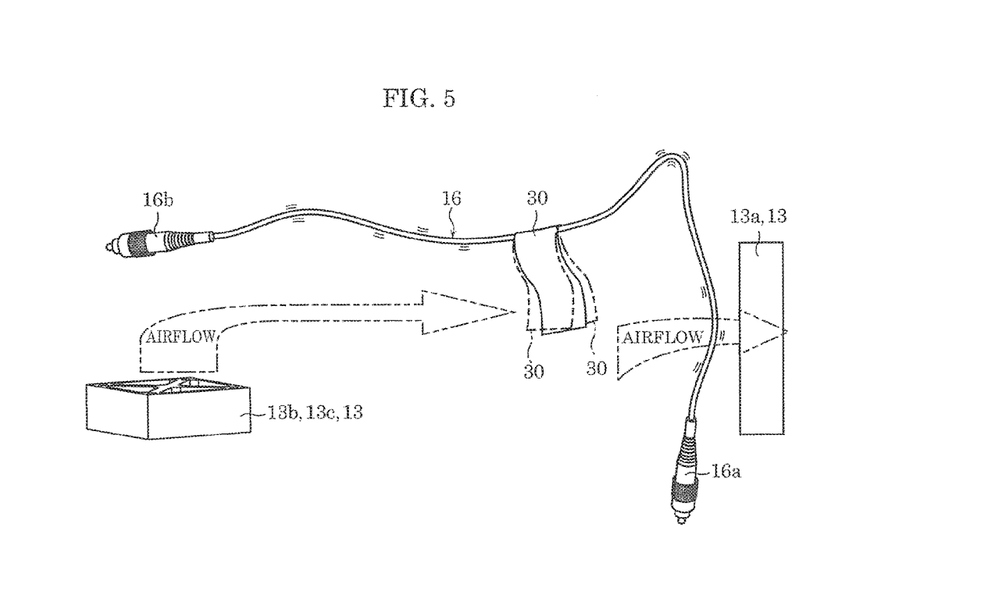
FIG. 5 is a schematic view illustrating the first fiber cable and a shakable body of the endoscope lighting device according to Embodiment 1.

FIG. 1 is a perspective view illustrating endoscope lighting device 10 according to the present embodiment. FIG. 2 is a plan view illustrating an inner structure of endoscope lighting device 10 according to the present embodiment. FIG. 3 is a block diagram illustrating endoscope lighting device 10 according to the present embodiment. FIG. 4 is a cross sectional view taken along line IV-IV in FIG. 2, illustrating, for example, first fiber cable 16 (an example of a fiber cable), fluorescent light emitter 15, and second fiber cable 17 of endoscope lighting device 10 according to the present embodiment. FIG. 5 is a schematic view illustrating first fiber cable 16 and shakable body 30 of endoscope lighting device 10 according to the present embodiment.

The X, Y, and Z directions indicate such directions that: in the direction in which first intake blower 13b and second intake blower 13c are arranged in housing 11, the side on which first intake blower 13b is disposed is the positive direction side of the X axis; the direction that is orthogonal to the positive direction of the X axis and is the direction from first intake blower 13b to exhaust blower 13a is the positive direction of the Y axis; and the direction orthogonal to the positive direction of the X axis and the positive direction of the Y axis is the positive direction of the Z axis. The directions shown in FIG. 1 all correspond to the directions shown in FIG. 2. The same applies to the subsequent figures following FIG. 2.

As illustrated in FIG. 1, endoscope lighting system 1 according to the present embodiment is used for an endoscope and includes endoscope lighting device 10, a plurality of second fiber cables 17, image transmission cable 24, tip end portion 25, and camera control unit 100. Camera control unit 100 is disposed on the positive side of the Z axis relative to endoscope lighting device 10.

One end of a cable group is connected to endoscope lighting device 10 and camera control unit 100. The cable group includes the plurality of second fiber cables 17 that transmit fluorescent light and image transmission cable 24 that transmits an image. The plurality of second fiber cables 17 and image transmission cable 24 are tied into a bundle as the cable group. Tip end portion 25 is provided to the other end (tip end) of the cable group. Portions inserted into a body, such as the cable group and tip end portion 25, are referred to as an endoscope.

As illustrated in FIG. 2 to FIG. 4, endoscope lighting device 10 includes housing 11, a plurality of laser light sources 14, a plurality of blowers 13, a plurality of fluorescent light emitters 15, a plurality of first fiber cables 16, device-side controller 18, and power source 19. Laser light sources 14, fluorescent light emitters 15, first fiber cables 16, device-side controller 18, power source 19, etc., are in housing 11 of endoscope lighting device 10.

As illustrated in FIG. 1 and FIG. 2, housing 11 is a rectangular casing and includes first cover 110 and second cover 111.

First cover 110 includes bottom portion 110a having an approximately rectangular plate shape, first wall portion 110b rising from one edge of bottom portion 110a, and second wall portion 110c rising from another edge of bottom portion 110a and approximately parallel to first wall portion 110b.

First cover 110 is a cover of housing 11 located on the negative side of the Z axis relative to housing 11, and is formed using a metal plate, for example. Laser light sources 14, a heat dissipating component (heat sink), blowers 13, power source 19, etc., are fixed to first cover 110. A plurality of inlet openings 112 through which the outside air enters are formed in bottom portion 110a of first cover 110, in the X axis direction along first wall portion 110b. In the present embodiment, two inlet openings 112 are formed.

Second cover 111 is a cover of housing 11 located on the positive side of the Z axis relative to housing 11, and is formed using a metal plate, for example. Second cover 111 covers first cover 110 from the positive side of the Z axis.

As illustrated in FIG. 2 to FIG. 4, each of laser light sources 14 is a device that emits laser light and allows the laser light to enter one end of corresponding first fiber cable 16. The laser light excites phosphors in fluorescent light emitters 15, and causes fluorescent light emitters 15 to emit fluorescent light. Specifically, laser light sources 14 are provided to bottom portion 110a of first cover 110, and are, in the present embodiment, disposed between exhaust blower 13a and first and second intake blowers 13b and 13c which will be described later. Laser light sources 14 are controlled by device-side controller 18.

Laser light sources 14 are fixed to bottom portion 110a of first cover 110 via the heat dissipating component (heat sink) attached to bottom portion 110a of first cover 110. The heat dissipating component conducts heat generated by laser light sources 14 to first cover 110. In the present embodiment, four laser light sources 14 are disposed on a surface of the heat dissipating component on the positive side of the Z axis. Note that the number of laser light sources 14 is not limited to four.

Laser light sources 14 may be semiconductor lasers that emit laser light in a range (wavelength band) from ultraviolet laser light, which is shorter in wavelength than blue laser light, to blue laser light, for example. Indium gallium nitride (InGaN) laser diodes or aluminum indium gallium nitride (AlInGaN) laser diodes, for example, can also be used as laser light sources 14.

In the present embodiment, the output of laser light is 0.7 (W), the energy conversion efficiency for laser light is 120 (lm/W), and the combining efficiency of converted pseudo white light is 12%, for example. In this case, the luminous flux at the tips of second fiber cables 17 is 10.08 (lm) (=0.7 (W)×120 (lm/W)×12%).

Blowers 13 are devices that generate airflow in housing 11 via air openings formed in housing 11, and are, for example, fans, pumps, or devices using these. Blowers 13 are controlled by device-side controller 18.

In the present embodiment, the plurality of blowers 13 include first intake blower 13b, second intake blower 13c, and exhaust blower 13a. That is to say, at least one of the plurality of blowers 13 is exhaust blower 13a, whereas at least other ones of the plurality of blowers 13 are first intake blower 13b and second intake blower 13c.

First intake blower 13b and second intake blower 13c generate airflow in housing 11 by taking air into housing 11 from outside housing 11. First intake blower 13b and second intake blower 13c are fixed to bottom portion 110a of first cover 110 on a side of bottom portion 110a closer to first wall portion 110b. Specifically, first intake blower 13b and second intake blower 13c are attached one-on-one to two inlet openings 112 formed in bottom portion 110a of first cover 110.

First intake blower 13b and second intake blower 13c take air into housing 11 toward the positive side of the Z axis in housing 11. Note that endoscope lighting device 10 has a case leg on a surface of bottom portion 110a of first cover 110 on the negative side of the Z axis, and the case leg creates a space between a plane on which endoscope lighting device 10 is disposed and bottom portion 110a. This space allows first intake blower 13b and second intake blower 13c to take in the outside air.

Exhaust blower 13a generates airflow in housing 11 by exhausting the air inside housing 11 to outside housing 11. Exhaust blower 13a is fixed to second wall portion 110c.

Exhaust blower 13a exhausts the air from housing 11 toward the positive side of the Y axis.

Each of fluorescent light emitters 15 is a wavelength converter that converts laser light passing through first fiber cable 16 into predetermined light (fluorescent light). Each fluorescent light emitter 15 includes a phosphor that emits fluorescent light using the laser light from first fiber cable 16. The phosphor is, for example, an yttrium aluminum garnet (YAG) phosphor or a BaMgAl (BAM) phosphor, and can be selected as appropriate according to the type of laser light emitted by laser light source 14. Moreover, the phosphor may be, for example, a red phosphor, a green phosphor, or a blue phosphor, and may emit, for example, red, green, or blue fluorescent light using the laser light.

As illustrated in FIG. 4, fluorescent light emitter 15 is a flat plate, and is disposed on first wall portion 110b of first cover 110, approximately parallel to the plane defined by the X axis and the Z axis. In other words, fluorescent light emitter 15 is disposed in close contact with light exit surface 116a of first fiber cable 16 such that the laser light exiting from light exit surface 116a passes through fluorescent light emitter 15, as well as in close contact with light entrance surface 117a of second fiber cable 17 such that the fluorescent light enters light entrance surface 117a.

In the present embodiment, each of fluorescent light emitters 15 is a multilayered structure formed by stacking, for example, sapphire, a dichroic mirror, a YAG phosphor, and liquid glass in sequence. The sapphire has anti reflective (AR) coat, and the AR-coated side of the sapphire is the light entrance surface of fluorescent light emitter 15 (light exit surface 116a side of first fiber cable 16).

In the present embodiment, fluorescent light emitter 15 is fixed in a space that is bowed inward in the positive direction of the Y axis from a surface of first wall portion 110b on the negative side of the Y axis. In other words, fluorescent light emitter 15 is disposed between receptacle 27 fixed to the surface of first wall portion 110b on the positive side of the Y axis and receptacle 28 fixed to a surface of first wall portion 110b on the negative side of the Y axis. In the present embodiment, four fluorescent light emitters 15 are provided to first cover 110 and they have the same configuration. Thus, description of the other fluorescent light emitters 15 is omitted.

Each of first fiber cables 16 is a fiber that receives the laser light emitted by corresponding laser light source 14, and is connected to a connector provided on laser light source 14 side and receptacle 27 fixed to a surface of first cover 110 on the positive side of the Y axis.

As illustrated in FIG. 2 and FIG. 4, each first fiber cable 16 includes first end connector 16a, second end connector 16b, and a first transmitter.

First end connector 16a is a connection terminal disposed on a first end side of first fiber cable 16. Second end connector 16b is a connection terminal disposed on a second end side of first fiber cable 16 opposite first end connector 16a. First end connector 16a is connected to laser light source 14, whereas second end connector 16b is connected to receptacle 27 fixed to the surface of first cover 110 on the positive side of the Y axis. In the present embodiment, second end connectors 16b are disposed in the positive direction of the Z axis relative to first intake blower 13b and second intake blower 13c. That is to say, airflow generated by first intake blower 13b and second intake blower 13c passes by second end connectors 16b. In the present embodiment, there are four laser light sources 14 having the same configuration, four receptacles 27 having the same configuration, and four receptacles 28 having the same configuration, and thus, description of the other first fiber cables 16 is omitted.

The first transmitter is a light-transmissive optical fiber including a material such as quartz glass or plastic. The first transmitter transmits the laser light emitted by corresponding laser light source 14. The laser light emitted by laser light source 14 enters the first transmitter via first end connector 16a, and the laser light passing through (transmitted by) the first transmitter exits the first transmitter via second end connector 16b opposite first end connector 16a.

Shakable body 30 causes first fiber cable 16 to shake at 60 Hz or greater. Since the camera frame rate is 60 Hz, it is possible to inhibit speckle noise from being included in the image when the oscillation frequency of first fiber cable 16 is 60 Hz or greater.

Each shakable body 30 is disposed corresponding to a different one of first fiber cables 16. Specifically, each shakable body 30 is fixed to first fiber cable 16 by a publicly known means such as an adhesive or pressure bonding. Each shakable body 30 is a component that shakes in reaction to the airflow generated by blowers 13, and has a shape of a band that flutters in reaction to the airflow. In the present embodiment, each shakable body 30 has a shape of a film or a tape, for example. The material of each shakable body 30 is, for example, a resin material such as celluloid or polyvinyl chloride, a fiber material such as a cloth or paper, or a metal film such as aluminum foil. That is to say, each shakable body 30 may have any material, structure, and shape, so long as it can flutter in reaction to airflow.

Each shakable body 30 may be curved. That is to say, each shakable body 30 is in such a shape that makes it easier to flutter in reaction to airflow generated in housing 11, so as to cause first fiber cable 16 to shake. In the present embodiment, each shakable body 30 has a wavy shape. That each shakable body 30 is curved basically means that shakable body 30 has a curved shape in a state of being at rest, although shakable body 30 may be curved when fluttering.

Each shakable body 30 is disposed at a lengthwise central portion of first fiber cable 16. In other words, each shakable body 30 is fixed to corresponding first fiber cable 16, at a position distant from first end connector 16a and second end connector 16b. Note that each shakable body 30 may be fixed to corresponding first fiber cable 16 in the vicinity of first end connector 16a or second end connector 16b. That is to say, the position of shakable body 30 is not limited to the central portion of first fiber cable 16.

Shakable bodies 30 are disposed in flow paths R (shown by a two-dot chain line in FIG. 2) between first intake blower 13b and exhaust blower 13a and between second intake blower 13c and exhaust blower 13a. That is to say, shakable bodies 30 are not disposed at positions distant from flow paths R generated by first intake blower 13b, second intake blower 13c, and exhaust blower 13a. In the present embodiment, flow paths R are formed along the lengthwise direction of first fiber cables 16. Note that flow paths R may intersect with first fiber cables 16.

Each shakable body 30 contacts a different one of first fiber cables 16. Each shakable body 30 contacting a different one of first fiber cables 16 is different in size. Although four shakable bodies 30 are provided in the present embodiment, the number of shakable bodies 30 is not limited to four because shakable bodies 30 may be provided according to the number of first fiber cables 16. Note that each shakable body 30 may be approximately the same in size; being different in size is not an essential requirement.

For example, shakable body 30 has a size on the order of 50 mm×10 mm and a thickness of 0.05 mm. In the present embodiment, there are four shakable bodies 30 having the same configuration, and thus, description of the other shakable bodies 30 is omitted.

Device-side controller 18 controls the light emission of the plurality of laser light sources 14 and the operation of the plurality of blowers 13 via power source 19. Device-side controller 18 includes, for example, a circuit for controlling laser light sources 14 and blowers 13. Device-side controller 18 achieves its operation using, for example, a microcomputer, a processor, or a dedicated circuit that controls current supplied to laser light sources 14, etc.

Power source 19 is fixed to first cover 110. Power source 19 is disposed adjacent to laser light sources 14, on the negative side of the X axis relative to laser light sources 14. Power source 19 includes a power source circuit that generates power for causing laser light sources 14 to emit light. Power source 19 is electrically connected to a power system by a control power line, for example. Power source 19 may include a driver circuit that is controlled by device-side controller 18 and supplies power to, for example, blowers 13 and laser light sources 14.

Each of second fiber cables 17 is a fiber that transmits fluorescent light, and is connected to tip end portion 25 and receptacle 28 fixed to the surface of first cover 110 on the negative side of the Y axis.

Each second fiber cable 17 includes first end connector 17a and a second transmitter.

First end connector 17a is disposed on a first end side of second fiber cable 17. First end connector 17a is connected to receptacle 28 fixed to the surface of first cover 110 on the negative side of the Y axis. Tip end portion 25 is disposed at a second end side of second fiber cable 17 opposite first end connector 17a. In the present embodiment, there are four receptacles 28, each of which is connected to a different one of second fiber cables 17.

The second transmitter is a light-transmissive optical fiber including a material such as quartz glass or plastic. The fluorescent light emitted by fluorescent light emitter 15 passes through (is transmitted by) the second transmitter. The fluorescent light emitted by fluorescent light emitter 15 enters the second transmitter via first end connector 17a, and the fluorescent light passing through the second transmitter exits the second transmitter via a second end portion (tip end portion 25) opposite first end connector 17a.

Note that the second transmitter is larger than the first transmitter in diameter in order for the fluorescent light emitted by fluorescent light emitter 15 to more efficiently enter the second transmitter. From a standpoint of the efficient entrance of the fluorescent light, a quartz fiber having a refractive index na of 0.22 is used for the first transmitter, whereas a multicomponent glass fiber having a refractive index na of 0.87 is used for the second transmitter, for example.

As described above, when first fiber cable 16 and second fiber cable 17 are connected to receptacle 27 and receptacle 28, respectively, fluorescent light emitter 15 is interposed between first fiber cable 16 and second fiber cable 17.

Camera control unit 100 processes an image captured by tip end portion 25. Camera control unit 100 includes, for example, image processor 100a, camera-side controller 100b, and storage 100c.

Second end portions of second fiber cables 17 and a second end portion of image transmission cable 24 are connected to tip end portion 25. Tip end portion 25 includes camera 26 that captures an image of an object.

Camera 26 is a charge-coupled device (CCD) camera, for example. Camera 26 transmits a signal of the captured image of the object to image processor 100a of camera control unit 100 via image transmission cable 24. Image processor 100a performs appropriate image processing by converting the input signal of the image into image data, so as to generate output image information desired. The image information generated is then displayed on a display via camera-side controller 100b as an observation image of the endoscope. Moreover, as necessary, camera-side controller 100b stores the image information in storage 100c that includes memory, for example.

With such endoscope lighting device 10 as described above, airflow is generated in housing 11 when first intake blower 13b, second intake blower 13c, and exhaust blower 13a operate. Specifically, flow path R is generated between first intake blower 13b and exhaust blower 13a, and another flow path R is generated between second intake blower 13c and exhaust blower 13a. Shakable bodies 30 disposed in these flow paths R flutter in reaction to the airflow. As shakable bodies 30 flutter, first fiber cables 16 connected to shakable bodies 30 shake irregularly. The irregular shake of first fiber cables 16 causes a temporal variation in the pattern of speckles of the light entering or exiting from first fiber cables 16. More specifically, with the irregular shake of first fiber cables 16: first end connectors 16a shake, causing an irregular variation in the pattern of the laser light entering first end connectors 16a; and second end connectors 16b shake, causing an irregular variation in the pattern of the laser light exiting from second end connectors 16b. With this, endoscope lighting device 10 can inhibit speckles.

Advantageous Effects

Next, advantageous effects of endoscope lighting device 10 according to the present embodiment will be described.

As described earlier, endoscope lighting device 10 according to the present embodiment is used for an endoscope. Endoscope lighting device 10 includes: housing 11; laser light source 14 in housing 11; first fiber cable 16 that receives laser light emitted by laser light source 14; a phosphor of fluorescent light emitter 15 that emits fluorescent light using the laser light exiting from first fiber cable 16; blower 13 that generates airflow in housing 11; and shakable body 30 that contacts first fiber cable 16 and shakes in reaction to the airflow generated by blower 13.

Since shakable body 30 shaking in reaction to the airflow generated by blower 13 causes first fiber cable 16 to shake, speckles of the light entering or exiting from first fiber cable 16 can be inhibited.

With endoscope lighting device 10, since shakable body 30 causes first fiber cable 16 to shake, there is no need to add a piezoelectric element or the like that causes first fiber cable 16 to shake. Thus, the manufacturing cost of endoscope lighting device 10 is less likely to rise.

As such, it is possible to inhibit generation of speckles while inhibiting a rise in the manufacturing cost of endoscope lighting device 10.

In endoscope lighting device 10 according to the present embodiment, shakable body 30 has a shape of a band that flutters in reaction to airflow.

Since shakable body 30 has a shape of a band, shakable body 30 easily flutters in reaction to airflow. Thus, with endoscope lighting device 10, shakable body 30 can cause first fiber cable 16 to shake more. As a result, endoscope lighting device 10 can inhibit generation of speckles. In particular, since shakable body 30 having a band shape easily shakes in an irregular manner, it is suitable for inhibiting generation of speckles.

In endoscope lighting device 10 according to the present embodiment, shakable body 30 is curved.

Since shakable body 30 is curved, shakable body 30 easily flutters in small motions in reaction to airflow. Thus, with endoscope lighting device 10, shakable body 30 can cause first fiber cable 16 to shake more. As a result, endoscope lighting device 10 can more effectively inhibit generation of speckles.

In endoscope lighting device 10 according to the present embodiment, shakable body 30 includes a plurality of shakable bodies 30, and first fiber cable 16 includes a plurality of first fiber cables 16 with which the plurality of shakable bodies 30 contact. The plurality of shakable bodies 30 include shakable bodies 30 of different sizes.

Since each shakable body 30 contacting a different one of a plurality of first fiber cables 16 is different in size, each shakable body 30 flutters differently. Thus, each first fiber cable 16 shakes at a different oscillation frequency. That is to say, when each shakable body 30 is different in size, each first fiber cable 16 can shake at a different oscillation frequency. As a result, since each first fiber cable 16 can shake at a different oscillation frequency (the periodicity of the shake is disordered), endoscope lighting device 10 can further inhibit generation of speckles.

In endoscope lighting device 10 according to the present embodiment, shakable body 30 causes first fiber cable 16 to shake at 60 Hz or greater.

When the oscillation frequency of first fiber cable 16 is 60 Hz or greater, it is possible to inhibit speckle noise from being included in an image.

In endoscope lighting device 10 according to the present embodiment, housing 11 includes inlet opening 112 through which the outside air enters. Blowers 13 include a plurality of blowers 13. At least one blower 13 among the plurality of blowers 13 is exhaust blower 13a that exhausts air in housing 11. Shakable body 30 is disposed in flow path R generated by inlet opening 112 and exhaust blower 13a.

Since shakable body 30 is disposed in flow path R generated in housing 11 by a plurality of blowers 13, shakable body 30 easily flutters in reaction to airflow. With this, shakable body 30 can cause first fiber cable 16 to shake more. As a result, endoscope lighting device 10 can more effectively inhibit generation of speckles.

In endoscope lighting device 10 according to the present embodiment, housing 11 includes inlet opening 112 through which the outside air enters. Blower 13 that generates the airflow in housing 11 is in inlet opening 112.

In endoscope lighting device 10 according to the present embodiment, flow path R is along the lengthwise direction of first fiber cable 16.

Variation of Embodiment 1

In the present variation, an endoscope lighting device will be described with reference to FIG. 6.

Figure 6:
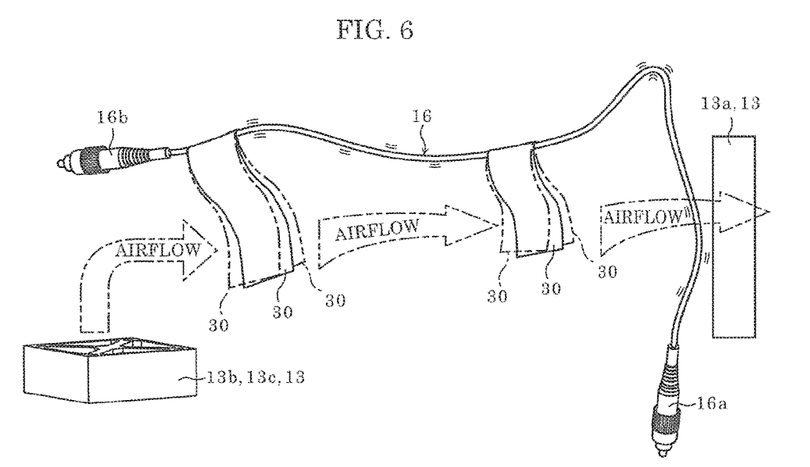
FIG. 6 is a schematic view illustrating a first fiber cable and shakable bodies of an endoscope lighting device according to a variation of Embodiment 1.

FIG. 6 is a schematic view illustrating first fiber cable 16 and shakable bodies 30 of the endoscope lighting device according to the present variation.

The present variation is different from Embodiment 1 in providing a plurality of shakable bodies 30 to first fiber cable 16.

The other structural elements of the endoscope lighting device according to the present variation are the same as those of endoscope lighting device 10 according to Embodiment 1. Unless otherwise noted, structural elements that are essentially the same share like reference signs, and detailed descriptions thereof are omitted.

A plurality of shakable bodies 30 contact first fiber cable 16. At least one of shakable bodies 30 may be disposed at a lengthwise central portion of first fiber cable 16, and at least a different one of shakable bodies 30 may be disposed at one of a first lengthwise end portion and a second lengthwise end portion of first fiber cable 16. In the present variation, one of shakable bodies 30 is disposed at the lengthwise central portion of first fiber cable 16, and a different one of shakable bodies 30 is disposed at the second lengthwise end portion of first fiber cable 16. Note that shakable body 30 may further be provided at the first lengthwise end portion of first fiber cable 16, or shakable body 30 may be provided at the second lengthwise end portion of first fiber cable 16 instead of shakable body 30 at the first lengthwise end portion of first fiber cable 16. That is to say, at least one shakable body 30 among the plurality of shakable bodies 30 is disposed at a lengthwise central portion of first fiber cable 16, and at least a different shakable body 30 among the plurality of shakable bodies 30 is disposed at one of a first end portion and a second end portion of first fiber cable 16.

In the present variation, a plurality of shakable bodies 30 contacting single first fiber cable 16 are of different sizes. Note that shakable bodies 30 contacting single first fiber cable 16 may be the same in size.

In the present variation, among two shakable bodies 30 contacting each first fiber cable 16, shakable body 30 disposed at the second lengthwise end portion of first fiber cable 16 is larger than shakable body 30 disposed at the lengthwise central portion. Note that the number of shakable bodies 30 is not limited to two, and three or more shakable bodies 30 may contact each first fiber cable 16.

In such an endoscope lighting device according to the present variation, a plurality of shakable bodies 30 contact each first fiber cable 16.

Since a plurality of shakable bodies 30 contact each first fiber cable 16, each first fiber cable 16 easily shakes as the plurality of shakable bodies 30 flutter. As a result, the endoscope lighting device can more effectively inhibit generation of speckles.

In particular, with the endoscope lighting device, since a plurality of shakable bodies 30 contact each first fiber cable 16, each first fiber cable 16 can easily shake in an irregular manner.

In the endoscope lighting device according to the present variation, at least one shakable body 30 among the plurality of shakable bodies 30 is disposed at a lengthwise central portion of first fiber cable 16, and at least a different shakable body 30 among the plurality of shakable bodies 30 is disposed at one of a first lengthwise end portion and a second lengthwise end portion of first fiber cable 16.

Since one shakable body 30 is provided at the lengthwise central portion of first fiber cable 16, first fiber cable 16 bends by a large amount. Thus, shake of shakable bodies 30 can be transmitted to first fiber cable 16.

Moreover, since shakable body 30 is also provided at the first lengthwise end portion or the second lengthwise end portion of first fiber cable 16, shake can be easily transmitted to first end connector 16a or second end connector 16b. As a result, the endoscope lighting device can more effectively inhibit generation of speckles.

In particular, with the endoscope lighting device, since shakable bodies 30 are disposed in at least two positions of each first fiber cable 16, each first fiber cable 16 can easily shake in an irregular manner.

In the endoscope lighting device according to the present variation, the different shakable body 30 disposed at the one of the first lengthwise end portion and the second lengthwise end portion of first fiber cable 16 is larger than the at least one shakable body 30 disposed at the lengthwise central portion of first fiber cable 16.

In the endoscope lighting device according to the present variation, shakable body 30 includes a plurality of shakable bodies 30, and first fiber cable 16 includes a plurality of fiber cables 16 with which the plurality of shakable bodies 30 contact. The plurality of shakable bodies 30 include shakable bodies 30 that are the same in size.

The advantageous effects of the present variation are the same as those of Embodiment 1, and detailed descriptions thereof are omitted.

Embodiment 2

In the present embodiment, endoscope lighting device 200 will be described with reference to FIG. 7.

Figure 7:
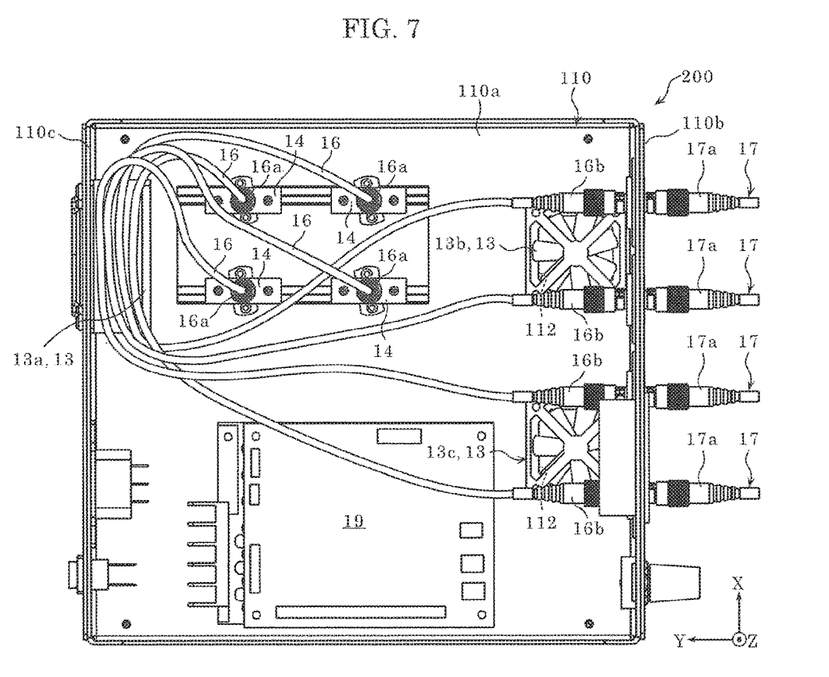
FIG. 7 is a plan view illustrating an inner structure of an endoscope lighting device according to Embodiment 2.

FIG. 7 is a plan view illustrating an inner structure of endoscope lighting device 200 according to the present embodiment.

As illustrated in FIG. 7, the present embodiment is different from Embodiment 1 in that shakable bodies 30 of Embodiment 1 are not used, and that first fiber cables 16 are in contact with exhaust blower 13*a*.

The other structural elements of endoscope lighting device 200 according to the present embodiment are the same as those of endoscope lighting device 10 according to Embodiment 1. Unless otherwise noted, structural elements that are essentially the same share like reference signs, and detailed descriptions thereof are omitted.

First fiber cables 16 are in contact with exhaust blower 13*a*. In other words, first fiber cables 16 are directly or indirectly in contact with exhaust blower 13*a* by being partially disposed along exhaust blower 13*a*. In the present embodiment, first fiber cables 16 are directly or indirectly in contact with a housing of exhaust blower 13*a*. That is to say, first fiber cables 16 are directly or indirectly in contact with exhaust blower 13*a* so that vibration of exhaust blower 13*a* is directly or indirectly transmitted to first fiber cables 16. Here, "indirectly in contact" means indirect contact between exhaust blower 13*a* and first fiber cables 16 via a component that transmits the vibration. Accordingly, one first fiber cable 16 may be indirectly in contact with another first fiber cable 16, and the component may be the sheath of first fiber cable 16 covering the first transmitter.

Note that first fiber cables 16 may be fixed to exhaust blower 13*a* using a fixing component so as not to be separated from exhaust blower 13*a*. A publicly known component such as a tape or an adhesive can be used as the fixing component.

Note that when disposing each first fiber cable 16 in direct or indirect contact with exhaust blower 13*a*, a transmission component may be provided between exhaust blower 13*a* and some of first fiber cables 16. Moreover, the material of the transmission component may be different for each first fiber cable 16. In this case, the oscillation frequency can vary for each first fiber cable 16.

Advantageous Effects

Next, advantageous effects of endoscope lighting device 200 according to the present embodiment will be described.

As described earlier, endoscope lighting device 200 according to the present embodiment is used for an endoscope. Endoscope lighting device 200 includes: housing 11; laser light source 14 in housing 11; first fiber cable 16 that receives laser light emitted by laser light source 14; a phosphor of fluorescent light emitter 15 that emits fluorescent light using the laser light exiting from first fiber cable 16; and blower 13 that generates airflow in housing 11. First fiber cable 16 is in contact with blower 13.

Since first fiber cables 16 are in contact with exhaust blower 13*a*, vibration caused by the operation of exhaust blower 13*a* is transmitted to first fiber cables 16. With this, first fiber cables 16 shake, and thus, speckles of the light entering or exiting from first fiber cable 16 can be inhibited.

With endoscope lighting device 200, since exhaust blower 13*a* causes first fiber cables 16 to shake, there is no need to add a piezoelectric element or the like that causes first fiber cable 16 to shake. Thus, the manufacturing cost of endoscope lighting device 200 is less likely to rise.

As such, it is possible to inhibit generation of speckles while inhibiting a rise in the manufacturing cost of endoscope lighting device 200.

In endoscope lighting device 200 according to the present embodiment, first fiber cable 16 is directly or indirectly in contact with exhaust blower 13*a* by being partially disposed along exhaust blower 13*a*.

In endoscope lighting device 200 according to the present embodiment, first fiber cable 16 is fixed in contact with exhaust blower 13*a*.

In endoscope lighting device 200 according to the present embodiment, first fiber cable 16 is in contact with exhaust blower 13*a* via a component that transmits vibration of exhaust blower 13*a*.

The advantageous effects of the present embodiment are the same as those of Embodiment 1, and detailed descriptions thereof are omitted.

Other Variations Etc

Hereinbefore, the present disclosure has been described based on Embodiments 1 and 2 and a variation of Embodiment 1, but the present disclosure is not limited to Embodiments 1 and 2 and the variation of Embodiment 1.

For example, in the above embodiments, the endoscope lighting device includes the first intake blower and the second intake blower, but the endoscope lighting device may include none of these blowers but include an inlet opening only. Even in this case, airflow can be generated in the housing because the air enters through the inlet opening when the exhaust blower operates.

Moreover, although the endoscope lighting device in the above embodiments is used for an endoscope, it may be used for a projector.

Hereinbefore, one or more aspects of the present disclosure have been described based on Embodiments 1 and 2 and a variation of Embodiment 1, but the present disclosure is not limited to Embodiments 1 and 2 and the variation of Embodiment 1. Various modifications to Embodiments 1 and 2 and the variation of Embodiment 1 conceived by those skilled in the art, as well as embodiments resulting from combinations of structural elements of different embodiments may be included within the scope of one or more aspects of the present disclosure, as long as such modifications and embodiments do not depart from the essence of the present disclosure.

While the foregoing has described one or more embodiments and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present teachings.

What is claimed is:

1. An endoscope lighting device to be used for an endoscope, the endoscope lighting device comprising:
   a housing;
   a laser light source in the housing;
   a fiber cable that receives laser light emitted by the laser light source;
   a phosphor that emits fluorescent light using the laser light exiting from the fiber cable;
   a blower that generates airflow in the housing; and
   a shakable body that contacts the fiber cable, shakes in reaction to the airflow generated by the blower, and transmits shake to the fiber cable.

2. The endoscope lighting device according to claim 1, wherein
   the shakable body has a shape of a band that flutters in reaction to the airflow in the housing.

3. The endoscope lighting device according to claim 2, wherein
   the shakable body is curved.

4. The endoscope lighting device according to claim 1, wherein
   the shakable body comprises a plurality of shakable bodies, and
   the plurality of shakable bodies contact the fiber cable.

5. The endoscope lighting device according to claim 4, wherein
   at least one shakable body among the plurality of shakable bodies is disposed at a lengthwise central portion of the fiber cable, and at least a different shakable body among the plurality of shakable bodies is disposed at one of a first lengthwise end portion and a second lengthwise end portion of the fiber cable.

6. The endoscope lighting device according to claim 5, wherein
   the different shakable body disposed at the one of the first lengthwise end portion and the second lengthwise end portion of the fiber cable is larger than the at least one shakable body disposed at the lengthwise central portion of the fiber cable.

7. The endoscope lighting device according to claim 1, wherein
   the shakable body comprises a plurality of shakable bodies,
   the fiber cable comprises a plurality of fiber cables with which the plurality of shakable bodies contact, and
   the plurality of shakable bodies include shakable bodies of different sizes.

8. The endoscope lighting device according to claim 1, wherein
   the shakable body comprises a plurality of shakable bodies,
   the fiber cable comprises a plurality of fiber cables with which the plurality of shakable bodies contact, and
   the plurality of shakable bodies include shakable bodies that are same in size.

9. The endoscope lighting device according to claim 1, wherein
   the shakable body causes the fiber cable to shake at 60 Hz or greater.

10. The endoscope lighting device according to claim 1, wherein
    the housing includes an inlet opening through which outside air enters,
    the blower comprises a plurality of blowers,
    at least one blower among the plurality of blowers is an exhaust blower that exhausts air in the housing, and
    the shakable body is disposed in a flow path generated by the inlet opening and the exhaust blower.

11. The endoscope lighting device according to claim 10, wherein
    the flow path is along a lengthwise direction of the fiber cable.

12. The endoscope lighting device according to claim 1, wherein
    the fiber cable is directly or indirectly in contact with the blower by being partially disposed along the blower.

13. The endoscope lighting device according to claim 12, wherein
    the fiber cable is fixed in contact with the blower.

14. The endoscope lighting device according to claim 12, wherein
    the fiber cable is in contact with the blower via a component that transmits vibration of the blower.

15. The endoscope lighting device according to claim 1, wherein
    the housing includes an inlet opening through which outside air enters, and
    the blower that generates the airflow in the housing is in the inlet opening.

16. The endoscope lighting device according to claim 1, wherein
    the fiber cable is configured to shake in response to the shakable body shaking and transmitting the shake to the fiber cable.

17. An endoscope lighting device to be used for an endoscope, the endoscope lighting device comprising:
    a housing;
    a laser light source in the housing;
    a fiber cable that receives laser light emitted by the laser light source;
    a phosphor that emits fluorescent light using the laser light exiting from the fiber cable; and
    a blower that generates airflow in the housing,
    wherein the fiber cable is in contact with the blower that generates the airflow, and receives shake from the blower, and
    the blower that generates the airflow in the housing vibrates, with vibration being transmitted from the blower to the fiber cable as the shake.

* * * * *